United States Patent [19]

Brown

[11] Patent Number: 5,490,832
[45] Date of Patent: Feb. 13, 1996

[54] CRANIAL TRACTION TONG CONVERTIBLE TO A HALO AND A METHOD OF APPLYING A HALO TO A PATIENT

[76] Inventor: Cameron C. Brown, 7 Downing Rd., Hanover, N.H. 03755

[21] Appl. No.: 446,538

[22] Filed: May 19, 1995

Related U.S. Application Data

[62] Division of Ser. No. 160,490, Dec. 1, 1993.

[51] Int. Cl.$^6$ ..................................... A61F 5/00
[52] U.S. Cl. ............................. 602/37; 602/17; 602/32; 602/36; 128/898
[58] Field of Search ............................ 602/32–37, 17–19; 606/54, 59; 128/898

[56] References Cited

U.S. PATENT DOCUMENTS

| 2,494,792 | 1/1950 | Bloom | 602/37 |
| 3,072,118 | 1/1963 | Standerwick et al. | 602/17 |
| 3,604,412 | 9/1971 | Gardner | 602/37 |
| 3,654,923 | 4/1972 | Crutchfield | 602/37 |
| 3,923,046 | 12/1975 | Heifetz | 602/37 |
| 3,957,040 | 5/1976 | Calabrese . | |
| 4,444,179 | 4/1984 | Trippi | 602/37 |
| 4,667,660 | 5/1987 | Eingorn | 602/37 |
| 5,062,415 | 11/1991 | Weatherby et al. | 602/17 |
| 5,156,588 | 10/1992 | Marcune et al. | 602/17 |
| 5,203,765 | 4/1993 | Friddle, Jr. | 602/17 X |
| 5,302,170 | 4/1994 | Tweardy | 602/17 |

FOREIGN PATENT DOCUMENTS

282126  9/1990  Germany .

*Primary Examiner*—Linda C. Dvorak
*Attorney, Agent, or Firm*—Ratner & Prestia

[57] ABSTRACT

A cranial securing device has now been developed which includes a plurality of threaded holes for receiving skull pins, and a plurality of threaded holes for receiving tong pins. In practice, the device may be positioned on the head of the patient for traction. A traction is then applied to the patient through the cranial securing device. Once the traction is removed from the patient, the device may be rotated about the tong pins and appropriately positioned for use as a halo, while the tong pins are in place. Once positioned, skull pins may be inserted through the device to affix the device to the patient's head. The tong pins can then be removed and the device can be used as a halo. Furthermore, the device is designed to be used either forwards or backwards, with the open end in the front of the patient or in the rear of the patient.

9 Claims, 6 Drawing Sheets

FIG. 8

CRANIAL TRACTION TONG CONVERTIBLE TO A HALO AND A METHOD OF APPLYING A HALO TO A PATIENT

This application is a division of application Ser. No. 08/160,490, filed Dec. 1, 1993.

BACKGROUND OF THE INVENTION

The present invention pertains to halo traction units, and particularly halos for use in securing the head of patient to a superstructure for holding the head of the patient in a fixed and rigid position with respect to the body of the patient, and to skull tongs for providing traction to a patient.

DESCRIPTION OF RELATED ART

There are applications in orthopaedic surgery, neurosurgery, and other medical treatments and operative procedures where a patient's head must be engaged and held in a predetermined position with respect to the patient's body. Very often, during healing of injuries involving fracture or dislocation of the cervical spine, a patient's head must be immobilized with respect to the patient's body in order to allow the fractured or dislocated bones to heal. For this purpose, halo traction units have been developed.

A halo traction unit is a generally circular or elliptical unit which encircles the head of a patient. The halo includes threaded holes to receive skull pins. The skull pins project through the halo via the threaded holes until they contact and firmly hold the skull of the patient. Recently, open-backed halos have been developed. These halos take the form of a truncated ellipse, and allow application while the patient is secured to a backboard or is otherwise in a prone position. The halo is then secured to a superstructure which is in turn secured to a vest worn by the patient. The vest, superstructure, and halo combine to totally immobilize the head of the patient.

A halo traction unit for immobilization of the neck of a patient is well described in U.S. patent application Ser. No. 07/963,442 to Lisa Tweardy filed on Oct. 19, 1992, which patent application has been allowed is incorporated herein by reference.

In other applications and medical treatments, it is desirable to apply traction to the cervical spine and body of a patient, in order to provide proper treatment of a patient's injuries. This is particularly true in the case of a compression fracture of the cervical spine. For this purpose, skull tongs have been developed.

Briefly, skull tongs are shaped in the form of a semi-circle or partial ellipse. The skull tongs include holes to receive tong pins. The skull tongs are secured to a patient's head by driving tong pins through threaded holes in the skull tongs, and into the patient's skull. The tong pins thereby secure the skull of the patient to the tongs because the tong pins are secured directly to the bone of the patient's skull. The tong pins are similar to skull pins but larger because of the higher force exerted on them when applying traction to a patient.

Once the skull tongs are secured to the patient's head, the patient is positioned with the body of the patient held securely while force is exerted on the skull tongs in a direction opposite the body of the patient. Generally, this can be performed by laying the patient on an appropriately equipped table. A rope or wire is then attached to the skull tongs and run through a pulley at the end of the table near the patient's head. Weights are then added to the rope or wire in order to apply pressure and traction to the patient.

One problem with prior halos and skull tongs is that multiple units are required to provide traction and to secure the patient's head for long term immobilization and treatment. Thus skull tongs would be used to provide traction for the patient and would then be removed and replaced by a halo unit to provide long term immobilization. Furthermore, as shown in the above referenced patent application, when an open-ended halo is applied to a patient, the pins holding the halo to the patient's skull are placed in the front portion of the halo and are driven into the forehead of the patient. Such skull pins have at least two shortcomings. First, the use of skull pins in the front of a patient's head can be psychologically distressing to the patient since they are constantly within the patient's field of view. Secondly, skull pin sites in the forehead tend to give rise to additional complications, including infection and other problems which can require several relocations of the pins. Accordingly, it would be desirable to have a halo and skull tongs which overcome these problems.

SUMMARY OF THE INVENTION

A cranial securing device has now been developed which includes a plurality of threaded holes for receiving skull pins, and a plurality of threaded holes for receiving tong pins. In practice, the device may be positioned on the head of the patient for traction. Traction is then applied to the patient through the cranial securing device. Once the traction is removed from the patient, the device may be rotated about the tong pins and appropriately positioned for use as a halo, while the tong pins are in place. Once positioned, skull pins may be inserted through the device to affix the device to the patient's head. The tong pins can then be removed and the device can be used as a halo. Furthermore, the device is designed to be used either forwards or backwards, with the open end in the front of the patient or in the rear of the patient.

DETAILED DESCRIPTION OF THE DRAWINGS

The cranial securing device of the present invention can be used either as a traditional halo, or as traditional skull tongs. Furthermore, due to the placement of holes for skull pins and tong pins in the device, the device may be first applied and used as skull tongs and subsequently rotated and used as a halo, when connected to a suitable superstructure and vest.

Figure 1:
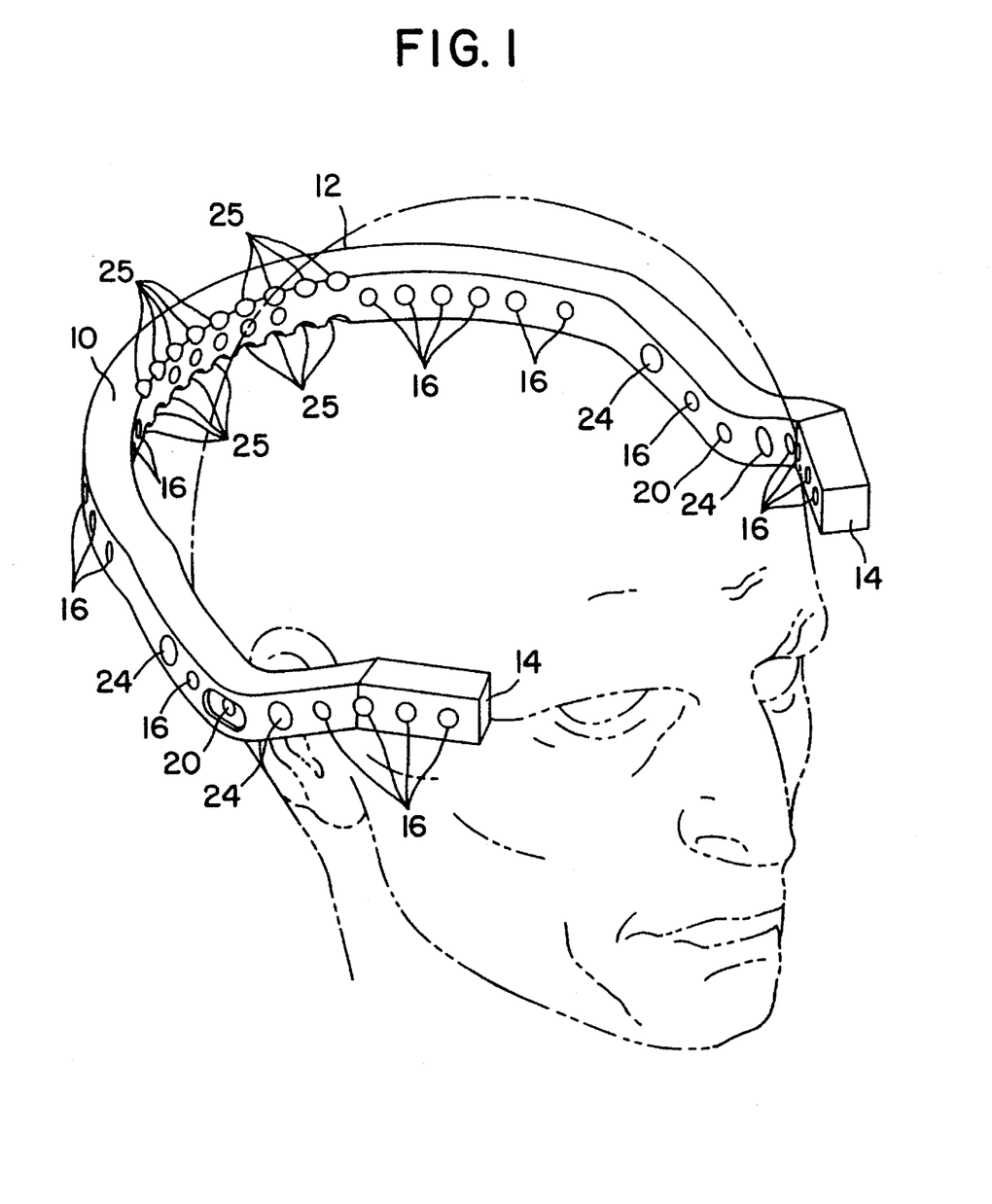
FIG. 1 is a perspective view of the device of the present invention applied to a patient with the opening positioned in the front of the patient.

Referring now to FIG. 1, cranial securing device 10 has a closed end 12 and an open end 14. Conventional application of open-ended cranial securing devices has been with the opening to the rear of the patient. However, by appropriate placement of skull pin receiving holes 16, cranial securing device 10 may be affixed to the head of a patient with open-end 14 in the front of the patient as shown in FIG. 1. By removing skull pins 18 from the forehead of the patient, complications which result from the placement of these pins is greatly reduced. Furthermore, scarring of the patient in visible areas is also reduced, as psychological trauma to the patient.

Figure 2A:
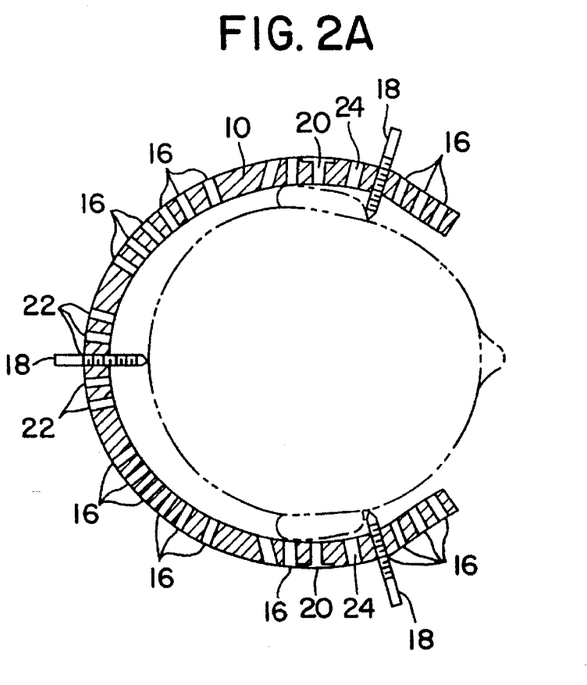
FIG. 2A is a top view of the device of the present invention applied to a patient with the opening positioned in the front of the patient.
Figure 2B:
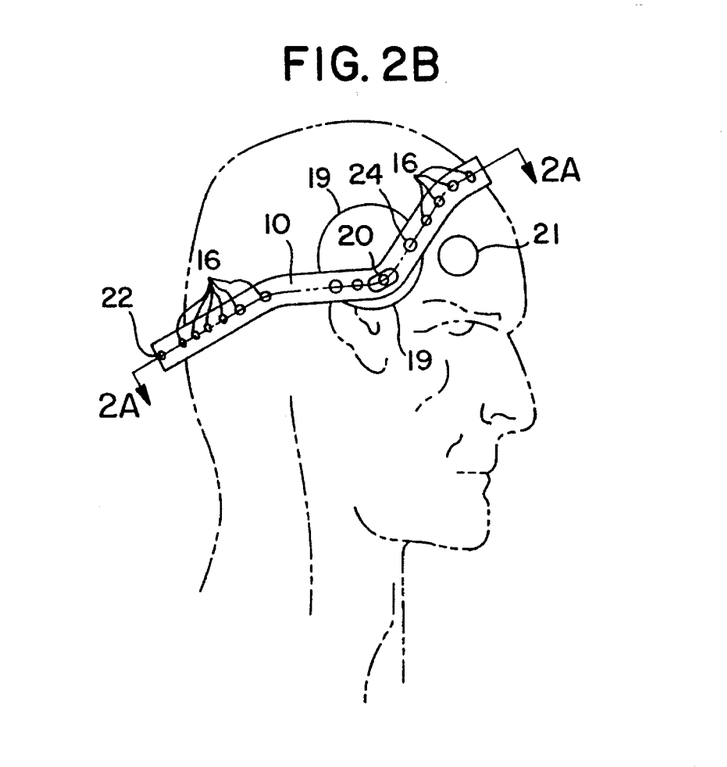
FIG. 2B is a side view of the device of the present invention applied to a patient with the opening positioned in the front of the patient.

Furthermore, by placing open end 14 to the front of the patient, cranial securing device 10 can be secured to the head of the patient with only three skull pins 18. Two of skull pins 18 are preferably located superior to the ear and posterior to the temporal muscle of the patient. The optimal region for placement of skull pins when cranial securing device 10 is secured with open end 14 to the front of the patient is region 19 shown in FIGS. 3 and 4. This placement is also shown in FIG. 2A. Preferably one skull pin 18 is located in the center of the rear of the patient's head, as will be explained presently. If cranial securing device is used with open end 14 in the rear of the patient, the optimal area for placement of skull pins 18 is area 21 as shown in FIGS. 2B and 4.

Placement of one skull pin in the rear portion of the head of the patient is most desirable in that only three skull pins 18 are needed. In prior art devices, four skull pins were often needed to securely fasten the device to the head of the patient. One fewer pin leads to commensurately fewer complications since there are fewer pin sites. However the portion of the rear of the head which is sufficiently strong to receive a skull pin is limited. That relatively thick and strong area of the head is a 3–4 centimeter wide rectangular strip of skull bordered superiorly by the maximal occipital point and extending inferiorly along the posterior midline to and including the inion. This area will be referred to as the posterior skull pin area.

Because the bone on the left and right sides of this region is very thin, it is important that rear skull pin receiving holes 22 are closely spaced in order to provide a plurality of pin sites in the posterior skull pin area. Accordingly, rear skull pin receiving holes 22 should be no more than 0.75 inches. Further, the group of five rear skull pin receiving holes should allow placement of skull pins 18 within a square 3½ centimeters on a side. In calculating the point where a skull pin would land, it is assumed that the cranial securing device 10 will be no more than one inch away from the head of the patient. Any suitable arrangement of skull pin receiving holes 22 would be acceptable. Further, a greater number of skull pin receiving holes 22 are desired to allow the greatest flexibility in placement of skull pins 18.

Figure 7:
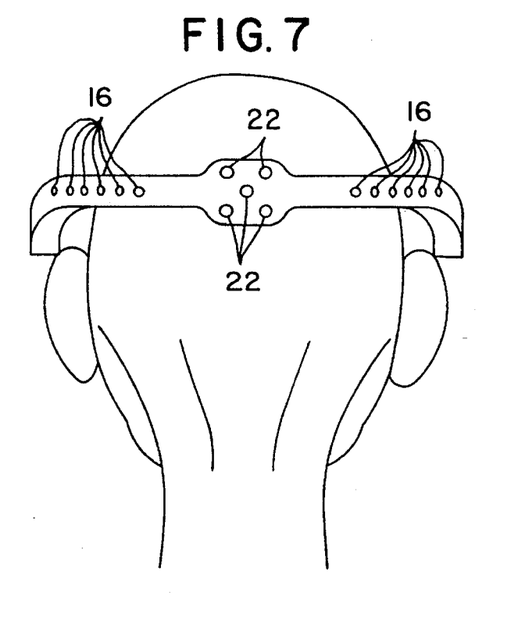
FIG. 7 is a rear view of a further embodiment of the present invention showing an alternative configuration of skull pin hole placement.

An alternative configuration for the rear of cranial securing device is shown in FIG. 7. In this configuration, skull pin receiving holes 22 are arranged in an "X" pattern to maximize both the distance between holes and the number of holes which can allow skull pins 18 to be placed in the posterior skull pin area.

Once cranial securing device 10 is secured to the head of the patient, the device may be attached to a superstructure and vest which is worn by the patient. This may be accomplished through superstructure receiving holes 20. The area around superstructure receiving hole 20 has been flattened in order to allow proper attachment of a superstructure to cranial securing device 10. In this way, combined with an appropriate superstructure and vest, cranial securing device 10 holds the head of a patient in a fixed predetermined spatial relationship to the body of the patient. This, of course, is the purpose of a cranial securing device, and the cervical spine of the patient is thereby allowed to heal.

As can be seen from FIGS. 2A, 2B, 3, and 4 cranial securing device 10 includes tong pin receiving holes 24. As can be seen from FIG. 2A, these tong pin receiving holes are angled slightly, in order to provide a better grip on the skull of the patient. Cranial securing device 10 can be used as a tong to provide traction to the patient as shown in FIG. 4. The cranial securing device 10 is positioned on a patient's head and tong pins (not shown) are inserted through tong pin receiving holes 24 and secured to the patient's skull. Traction can then be applied through cranial securing device 10.

Figure 3:
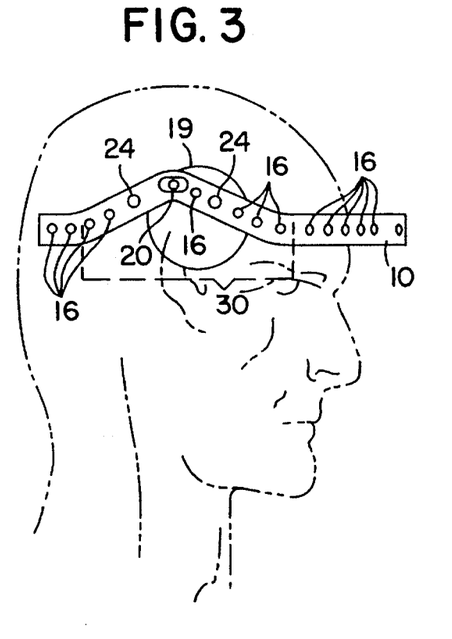
FIG. 3 is a side view of the device of the present invention applied to a patient with extended sections extending upwards from said device and with the opening in the rear of the patient's head.
Figure 4:
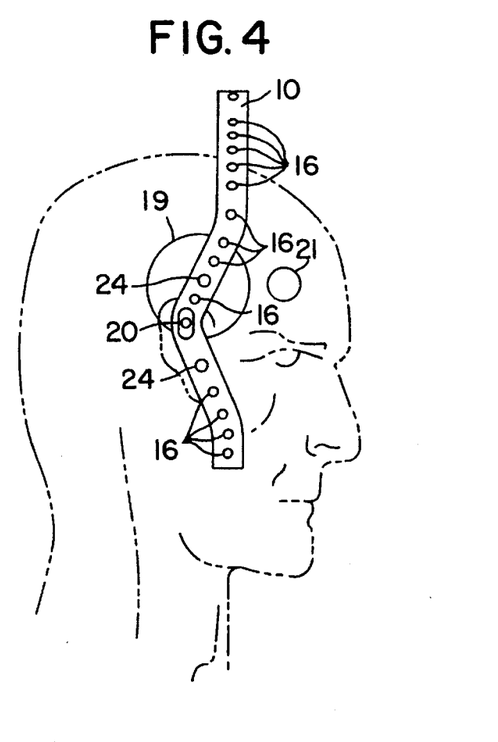
FIG. 4 is the device of the present invention applied to a patient to provide traction.

Once traction is removed, and long term immobilization is desired, cranial securing device can be rotated about the tong pins protruding through tong pin receiving holes 24, either to the position shown in FIG. 3 or the position shown in FIG. 2B. Once rotated, skull pins 18 are used to secure cranial securing device 10 to the patient's head in a horizontal position. All references to horizontal or vertical positions herein assume that the patient is sitting upright with the patient's head in a neutral alignment. Of course the device of the present invention will work in any position, but for reference purposes, horizontal and vertical positions will assume an upright patient.

Once skull pins 18 have been used to secure cranial securing device 10 in a horizontal position, the tong pins may be removed and a superstructure attached to cranial securing device 10. As shown in FIG. 3, cranial securing device 10 is generally flat with elevated section 30. Previously, halos similar to cranial securing device 10 have been used with elevated section 30 extending downwards from the plane of the remainder of the halo. This allowed the halo to be placed on the head of the patient while the skull tongs were in place. Since, as previously explained, cranial securing device 10 can be used both as a halo and as skull tongs for applying traction, the need for a second piece of equipment no long exists. Accordingly, cranial securing device 10 can be placed on the patient such that elevated section 30 extends upwards from the plane of the remainder of the halo. One advantage of this is that it does not interfere with the patient's ability to use a phone and other ordinary aural devices. Elevated section 30 can extend upwards both while open end 14 is at the rear of the patient as shown in FIG. 3, or if desired, while the open end 14 of cranial securing device 10 is placed in the front of the patient.

As described, the invention includes tong pin receiving holes 24 appropriately placed so that cranial securing device 10 can be used as skull tongs. However, cranial securing device 10 need not be fitted with tong pin receiving holes 24 if use as skull tongs is not desired. Instead, tong pin receiving holes 24 can be removed and replaced by an appropriate number of skull pin receiving holes. This will allow greater flexibility in placement of skull pins in the correct area 19 of the patient's skull.

Figure 5:
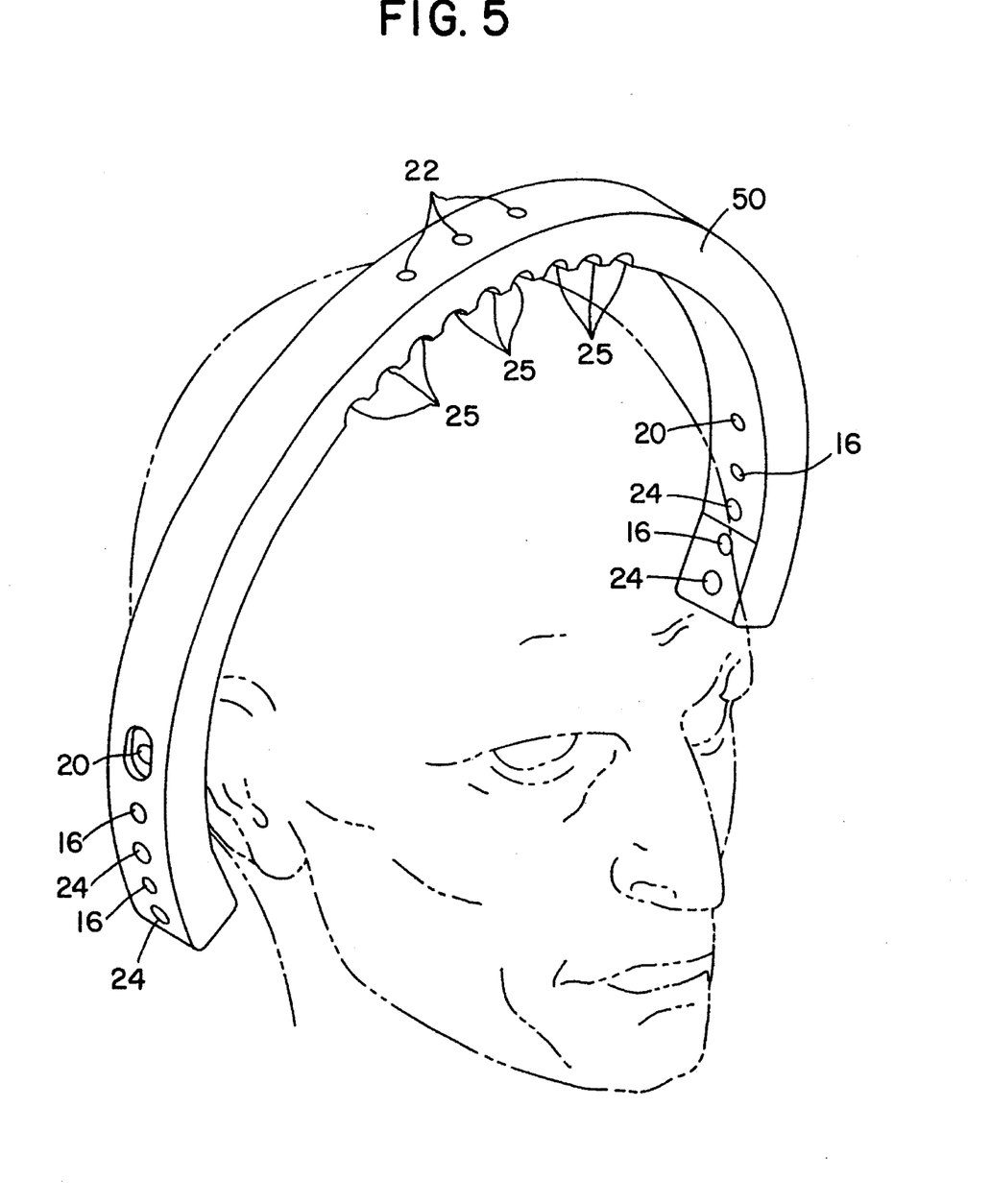
FIG. 5 is a perspective view of a second embodiment of the present invention applied to a patient and positioned to provide traction.
Figure 6A:
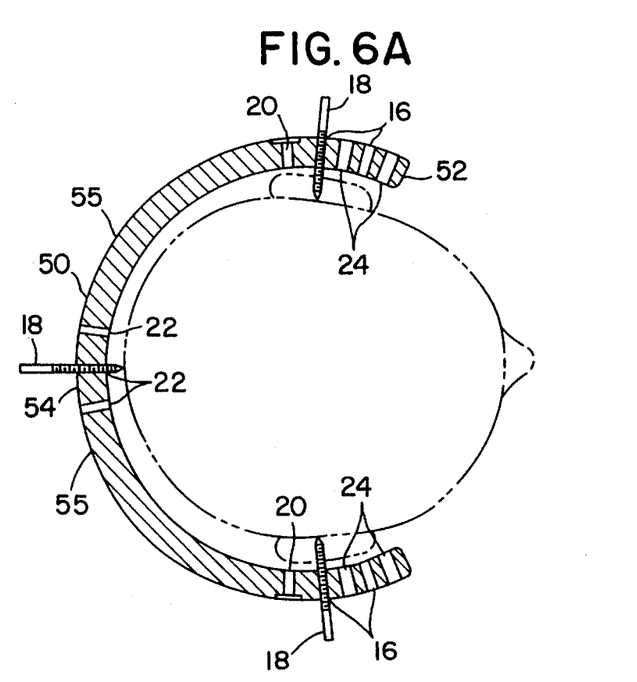
FIG. 6A is a top view of the second embodiment of the present invention applied to a patient with the opening to the front of the patient.
Figure 6B:
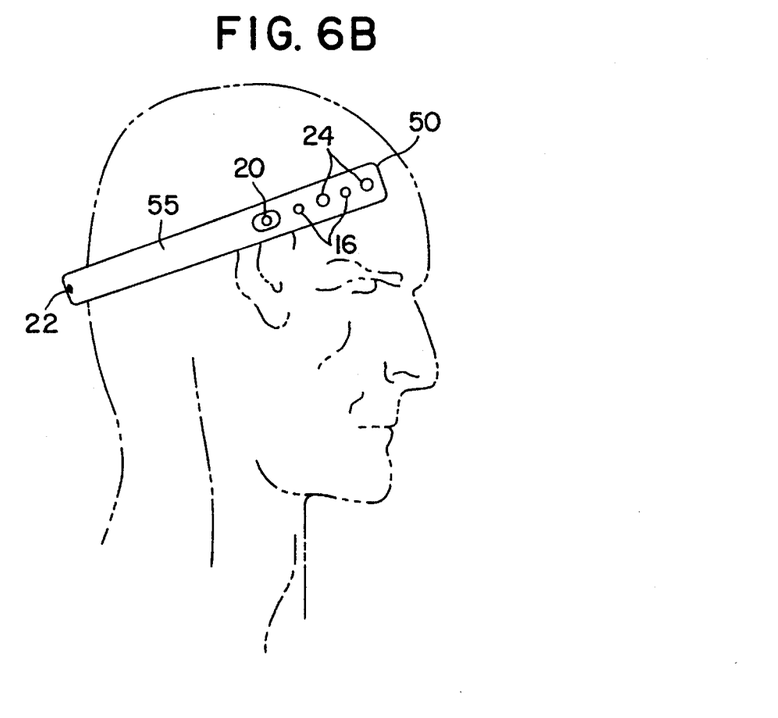
FIG. 6B is a side view of the second embodiment of the present invention applied to a patient with the opening to the front of the patient.

Alternatively, as shown in FIGS. 5, 6A and 6B, alternative cranial securing device 50 can be made without elevated section 30. Thus alternative cranial securing device 50 is in the shape of traditional skull tongs and has an open end 52 and a closed end 54. As may be seen from FIGS. 5, 6A and 6B, alternative cranial securing device 50 has fewer skull pin holes than cranial securing device 10. Without holes in area 55, alternative cranial securing device 50 should not be used with open end 52 toward the rear of the patient. This is because area 55 is normally where skull pins would be used to secure alternative cranial securing device 50 to a patient's forehead. Without skull pin receiving holes in area 55, it may be difficult or impossible to get an adequate rigid connection between alternative cranial securing device 50 and the head of the patient. However introduction of skull pin receiving holes into area 55 in appropriate positions, may enable the use of alternative cranial device 50 on a patient with open end 52 situated at the rear of the patient.

As may be seen from FIGS. 1 and 5 both cranial securing device 10 and alternative cranial securing device 50 include notches 25 for receiving a hook which may be used to apply traction to the patient when the securing device is used as skull tongs. Several notches 25 are provided on each cranial securing device 10 and 50 in order to provide multiple angles at which traction may be applied to the patient.

Figure 8:
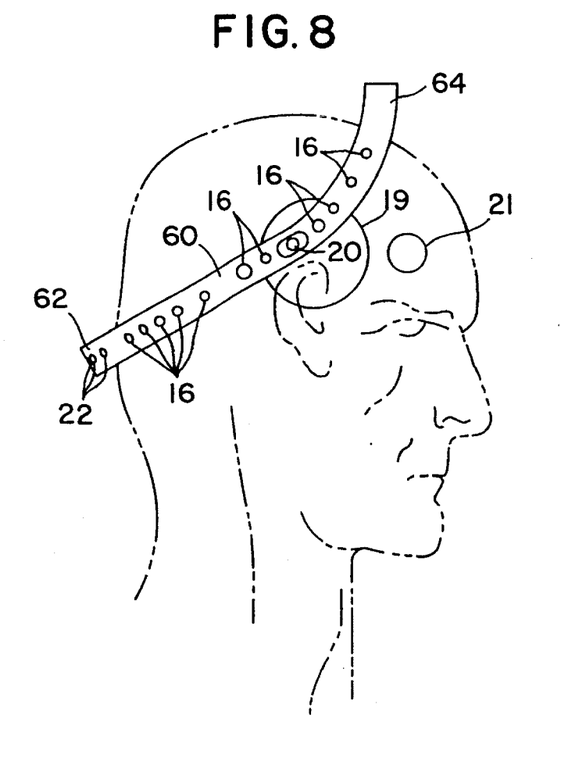
FIG. 8 is a side view of a further embodiment of the present invention including a closed ring halo.

FIG. 8 shows still another alternative embodiment of the present invention wherein a traditional closed ring cranial securing device 60 has been applied with the end 62 normally position to the front of the patient, now positioned to the patient's rear. This can be accomplished once placement of skull pin receiving holes 22 have been placed to ensure skull pins 18 will contact the posterior skull pin area. As can be seen from FIG. 8, this placement results in elevated end 64 being up and out of the field of view of the patient. This has significant psychological benefits to the patient. Furthermore, this placement allows affixation of the ring without placement of skull pins in the forehead of the patient, in area 21.

It is understood that various other modification will be apparent to an and can be readily made by those skilled in the art without departing from the spirit and scope of this invention. Accordingly, it is not intended that the scope of claims appended hereto be limited to the description as set forth herein, but rather that the claims be construed as encompassing all the features of patentable novelty that reside in the present invention, including all features that would be treated as equivalence thereof by those skilled in the art to which this invention pertains.

What is claimed:

1. A method of alternatively applying traction and immobilization to a patient with a single cranial device comprising:

affixing an open-ended cranial securing device to the head of the patient using tong pins;

applying traction to said patient;

removing traction from the patient;

rotating said device about said tong pins until said device is positioned horizontally when the head is in an upright position;

affixing said device to the head of the patient using skull pins; and removing said tong pins.

2. The method of claim 1 including rotating said device about said tong pins until said device is positioned horizontally when the head is in an upright position, and the openend of the device is positioned across the forehead of the patient.

3. The method of claim 2 wherein said open-ended cranial securing device is generally planar and includes two elevated sections, with coplanar sections on both sides of each said elevated section, said method including rotating said device about said tong pins until said device is positioned horizontally when the head is in an upright position and said elevated sections extend downwards from said device.

4. The method of claim 2 wherein said open-ended cranial securing device is generally planar and includes two elevated sections, with coplanar sections on both sides of each said elevated section, said method including rotating said device about said tong pins until said device is positioned horizontally when the head is in an upright position and said elevated sections extend upwards from said device.

5. The method of claim 1 including rotating said device about said tong pins until said device is positioned horizontally when the head is in an upright position, and the openend of the device is positioned across the occupant of the patient.

6. The method of claim 5 wherein said open-ended cranial securing device is generally planar and includes two elevated sections, with coplanar sections on both sides of each said elevated section, said method including rotating said device about said tong pins until said device is positioned horizontally when the head is in an upright position and said elevated sections extend downwards from said device.

7. The method of claim 5 wherein said open-ended cranial securing device is generally planar and includes two elevated sections, with coplanar sections on both sides of each said elevated section, said method including rotating said device about said tong pins until said device is positioned horizontally when the head is in an upright position and said elevated sections extend upwards from said device.

8. The method of claim 1 wherein said open-ended cranial securing device is generally planar and includes two elevated sections, with coplanar sections on both sides of each said elevated section, said method including rotating said device about said tong pins until said device is positioned horizontally when the head is in an upright position and said elevated sections extend downwards from said device.

9. The method of claim 1 wherein said open-ended cranial securing device is generally planar and includes two elevated sections, with coplanar sections on both sides of each said elevated section, said method including rotating said device about said tong pins until said device is positioned horizontally when the head is in an upright position and said elevated sections extend upwards from said device.

* * * * *

UNITED STATES PATENT AND TRADEMARK OFFICE
CERTIFICATE OF CORRECTION

PATENT NO. : 5,490,832
DATED : February 13, 1996
INVENTOR(S) : Brown

It is certified that error appears in the above-indentified patent and that said Letters Patent is hereby corrected as shown below:

Column 6, line 10, "openend" should be --open-end--.
Column 6, line 29, "openend" should be --open-end--.
Column 6, line 29, "occupant" should be --occiput--.

Signed and Sealed this

Twenty-third Day of July, 1996

*Attest:*

BRUCE LEHMAN

*Attesting Officer*          *Commissioner of Patents and Trademarks*